(12) United States Patent
Lenz

(10) Patent No.: US 8,507,049 B2
(45) Date of Patent: Aug. 13, 2013

(54) METHOD AND COMPOSITIONS FOR CREATING AN ATOMIC COMPOSITE OF CERAMICS COATED WITH TITANIUM MAKING USE OF COATING METHODOLOGY

(75) Inventor: Sorin Lenz, Salzburg (AT)

(73) Assignee: Ceramoss GmbH (AT)

( * ) Notice: Subject to any disclaimer, the term of this patent is extended or adjusted under 35 U.S.C. 154(b) by 420 days.

(21) Appl. No.: 12/918,791

(22) PCT Filed: Feb. 19, 2009

(86) PCT No.: PCT/EP2009/051999
§ 371 (c)(1),
(2), (4) Date: Nov. 12, 2010

(87) PCT Pub. No.: WO2009/103775
PCT Pub. Date: Aug. 27, 2009

(65) Prior Publication Data
US 2011/0052834 A1    Mar. 3, 2011

(30) Foreign Application Priority Data
Feb. 20, 2008  (EP) .................................. 08151711

(51) Int. Cl.
| C08J 7/06 | (2006.01) |
| F42B 10/00 | (2006.01) |
| A61K 6/083 | (2006.01) |
| B05D 3/00 | (2006.01) |

(52) U.S. Cl.
USPC . 427/509; 427/249.19; 427/250; 427/255.36; 427/561; 427/2.26; 102/514; 102/517; 86/51

(58) Field of Classification Search
USPC ......................................... 102/514, 516–520
See application file for complete search history.

(56) References Cited

U.S. PATENT DOCUMENTS 4,353,302 A * 10/1982 Strandli et al. ................ 102/364
5,340,058 A *  8/1994 Holl et al. ................. 244/117 A
(Continued)

FOREIGN PATENT DOCUMENTS

DE   102004041687 A1   4/2006
EP      0406021 A2    1/1991
(Continued)

OTHER PUBLICATIONS

Bagno, A. et al. "Surface Treatments and roughness properties of Ti-based biomaterials." Journal of Materials Science: Materials in Medicine. Kluwer Academic Publishers, BO., Bd. 15, No. 9, Sep. 2004, pp. 935-949.

(Continued)

Primary Examiner — Michael Cleveland
Assistant Examiner — Joel Horning
(74) Attorney, Agent, or Firm — Kolisch Hartwell, PC

(57) ABSTRACT

The invention relates to a method for the coating of a surface of a ceramic basic body with a titanium compound, comprising the steps of (i) providing a preformed ceramic material; (ii) at least one step of surface activation of said ceramic material using a plasma for plasma-chemical surface preparation wherein the plasma comprises high-energy ions; (iii) at least one step of applying a titanium compound bonding layer to said ceramic material by plasma-supported coating wherein the plasma-supported coating is performed in pulsed and/or non-pulsed fashion; (iv) at least one step of applying a functional titanium compound layer by pulsed plasma-supported coating. The invention also relates to novel compositions as well as uses of the novel compositions.

20 Claims, 15 Drawing Sheets

(56) References Cited

U.S. PATENT DOCUMENTS

Figure 1:
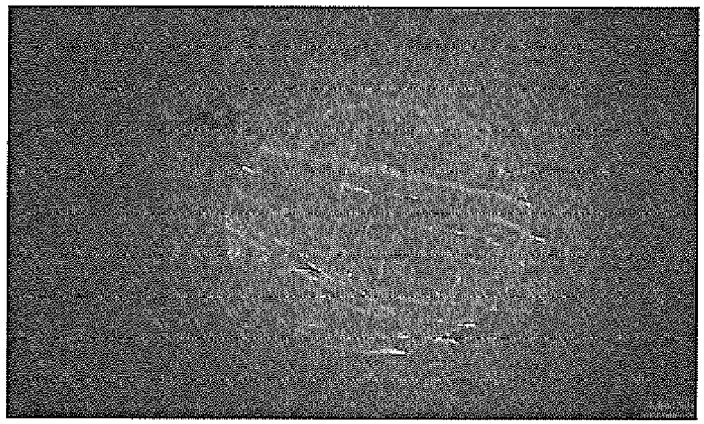

| | | | |
|---|---|---|---|
| 5,546,365 A | 8/1996 | Roth | |
| 6,374,743 B1 | 4/2002 | Hug et al. | |
| 2001/0036530 A1 | 11/2001 | Noda et al. | |
| 2003/0175444 A1 | 9/2003 | Huang et al. | |
| 2005/0106534 A1* | 5/2005 | Gahlert | 433/173 |
| 2006/0062912 A1 | 3/2006 | Wortman et al. | |

FOREIGN PATENT DOCUMENTS

| | | |
|---|---|---|
| EP | 0606566 A1 | 7/1994 |
| EP | 0676761 A1 | 10/1995 |
| EP | 0694918 A2 | 1/1996 |
| EP | 0737974 A2 | 10/1996 |
| GB | 2219886 A | 12/1989 |
| JP | 1021054 A | 1/1989 |
| WO | 96/39943 A1 | 12/1996 |
| WO | 03/045268 A1 | 6/2003 |

OTHER PUBLICATIONS

Franchi, M. et al. "Early detachment of titanium particles from various different surfaces of endosseous dental implants." Biomaterials, Elsevier Science Publishers BV., Bd. 25, No. 12, May 2004, pp. 2239-2246.
Frosch, Karl-Heinz et al. "Metallic Biomaterials in Skeletal Repair." European Journal of Trauma, Bd. 32, No. 2, Apr. 2006, pp. 149-169.
Geis-Gerstorfer, J. et al. "Geringere Oxidationsneigung unter Schutzgasatmosphäre." Dent. Lab. 1994, vol. 42, pp. 1235-1236.
Gilbert, J.L. et al. "Bond characteristics of porcelain fused to milled titanium." Dent. Mater. 1994, vol. 10, No. 2, pp. 134-140.
Könönen, M. and J. Kivilahti. "Bonding of low-fusing dental porcelain to commercially pure titanium." J. Biomed. Mater. Res. 1994, vol. 28, No. 9, pp. 1027-1035.
Könönen, M. and J. Kivilahti. "Fusing of dental ceramics to titanium." J. Dent. Res. 2001, vol. 80, No. 3, pp. 848-854.
Tesch, U. et al. "Untersuchungen zum Titan-Keramik-Verbund." Dent. Lab. 1993, vol. 41, pp. 71-74.
Tinschert, J. et al. "Struktur von Keramiken für die Titanverblendung." Dtsch. Zahnärztl Z 1995, vol. 50, pp. 31-34.
European Search Report dated Feb. 12, 2010 in connection with related European Application No. 08 15 1711.
European Search Report dated Dec. 5, 2007 in connection with related European Application No. 07 01 4516.

* cited by examiner

METHOD AND COMPOSITIONS FOR CREATING AN ATOMIC COMPOSITE OF CERAMICS COATED WITH TITANIUM MAKING USE OF COATING METHODOLOGY

FIELD OF THE INVENTION

This invention is in the field of ceramics and ceramic production. The invention is in particular in the field of ceramics with titanium surface layers. Such ceramics with one or more titanium surface layers according to the invention may be used as dental implants comprising for example an anchoring part for anchoring within the bone and comprising a mounting part for receiving an element to be attached, such as an abutment or a crown, a bridge or a prosthesis construction. However, the invention also relates to other applications of the ceramic titanium combination, such as its use in the field of ammunition or projectiles.

BACKGROUND OF THE INVENTION

Dental implants have been successfully used since more than 10 years. The major part of the dental implants currently used consist of titanium, since titanium has a sufficiently low elastic modulus and also has a relatively large strength. In addition, it is of particular importance that when using titanium as an implant material a safe integral osteogenesis can be reached when the surface is suitably treated (e.g. roughened by sand blasting). This means that the titanium implants, after reaching a primary stability by screwing into the bone, safely ossify within a healing time of about 3 to 4 months so that a permanent bond between the anchoring part screwed into the bone and the bone is guaranteed. Usually two-part implants are utilized. Basically, there are to possibilities for this end:

According to a closed sub gingival system the anchoring part of the implant is embedded until the bone ridge so that the mucoperiost cover can be sewn above the implant. A drawback is the necessary secondary operation at the end of the primary healing phase for allowing a subsequent application of a mounting part and thereon the desired prosthesis or crown.

By contrast, when using the open transgingival system, then the anchoring part of the implant can be sunk in up to about 3-5 mm above the bone ridge at mucosal level, thus avoiding a secondary operation. The wound edges can be directly adapted to the implant neck portion, thereby effecting a primary soft tissue closure to the implant.

Ceramic abutments offer particular advantages during the subsequent matching of the supra-construction, such as bridges or crowns, to the abutment. They can be simply ground and allow to build constructions using prior art processes known to the dentist. Ceramic abutments offer particular advantages due to the fact that their color can be closely matched to the natural tooth color. Lately also abutments of zirconia have been developed which offer a particularly high strength.

Such a system consisting of two-part implants having an anchoring part and a mounting part, an abutment and a prosthesis applied thereon offers a good matching to the geometric situation for different indications, however, generally the multitude of the components used is detrimental for the mechanical stability of the total system. Also each further bonding leads to possible starting points for bacteria which may cause parodontitis or gingivitis with the gap.

Lately also zirconia ceramics have become available that have an extremely high strength, in particular when the shaped bodies are prepared by hot isostatic pressing or by subsequent hot isostatic densifying. Such a zirconia ceramic which may roughly comprise 92.1-93.5 wt.-% $ZrO_2$, 4.5-5.5 wt.-% $Y_2O_3$ and 3.8-2.2 wt.-% $HfO_2$ is for instance known from U.S. Pat. No. 6,165,925.

However, the application of zirconia ceramic as a material for making the anchoring part of an implant seems not possible, since a sufficient mechanical stability of a zirconia ceramic is necessary, this requiring a highly dense preparation, practically without any porosity to be measured, this simultaneously leading to a clean cut extremely hard surface.

Such a material is bio-inert, so that no integrating osteogenesis is to be expected, this is why this material is not regarded to be suitable for the preparation of an anchoring part of an implant. In contrast, it is known that titanium covered ceramic shows extremely good results with respect to integrating osteogenesis. WO03/045268 discloses a dental implant wherein the anchoring part and the mounting part are configured in one piece from a zirconium oxide-based material. In principle titanium covered ceramic would be the material of choice. However, the formation of a strong bonding between the titanium layer and the ceramic has been a problem. This problem was in parts addressed in US 2001/0036530 A1. However, the results achieved by the methods disclosed in US 2001/0036530 A1 are not satisfactory. When the bonding strength is measured in five individual tests there are no cracks observed but the bonding strength of 67 MPa on average is only an insufficient step of over the methodology known in the prior art which will give a bonding strength of 41 MPa.

In particular there are applications of ceramic titanium combinations which require extremely high bonding strengths. Such applications are not just dental applications but also other medical applications such as bipolar hemiprostheses which are widely used for the treatment of medical fractures of the femoral neck in old patients with limited life expectancy since they allow for the surgical trauma to be reduced, and involve short rehabilitation times. The typical long-term problems encountered with such types of prostheses consist in polyethylene wear and destruction of the cartilage in the acetabulum, which as a consequence causes protrusion into the minor pelvis. In conventional dual-head prosthesis, the polyethylene used in the internal joint is subject to high mechanical strain which generally exceeds the strain rated for the material use. The accelerated wear resulting from this causes loss of sliding capacity of the internal joint, and hence prepares the way for technical failure of the conventional dual-head prosthesis. Also a ceramic dual-head prosthesis does not solve the problem. In theory, it allows for the friction inside the joint to be minimized, however, in practice such dual-ceramic prosthesis produce creaking noises and other unpleasant noises. It would therefore be advantageous to have ceramic compositions comprising titanium layers which may be used in such bipolar hemiprosthesis and which have a satisfactory bonding strength between the titanium layer and the ceramic unit thereby allowing for such applications.

The present invention solves the problems outlined above by providing for a method which leads to an extreme bonding strength between a given ceramic unit and its titanium layer.

SUMMARY OF THE INVENTION

The present invention relates to a method for the coating of a surface of a ceramic basic body with a titanium compound, comprising the steps of (i) providing a preformed ceramic material; (ii) at least one step of surface activation of said ceramic material using a plasma for plasma-chemical surface preparation wherein the plasma comprises high-energy ions; (iii) at least one step of applying a titanium compound bonding layer to said ceramic material by plasma-supported coating wherein the plasma-supported coating is performed in an pulsed and/or non-pulsed fashion; (iv) at least one step of applying a functional titanium compound layer by pulsed plasma-supported coating.

The invention also relates to novel compositions as well as uses of the novel compositions.

FIGURE CAPTIONS

Figure 2:
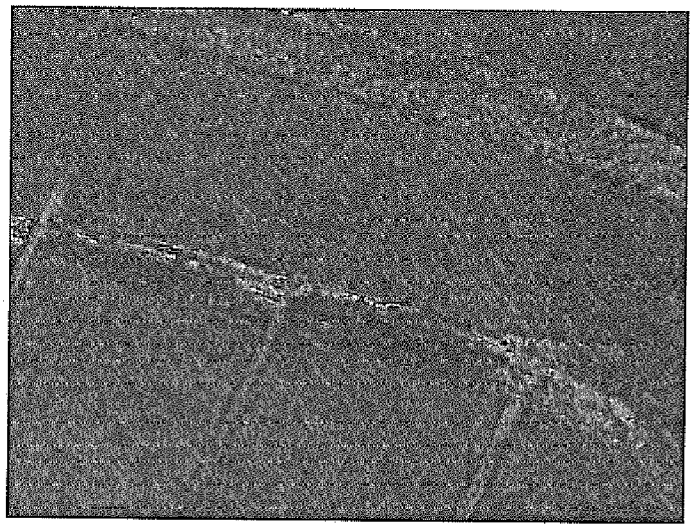
Figure 3:
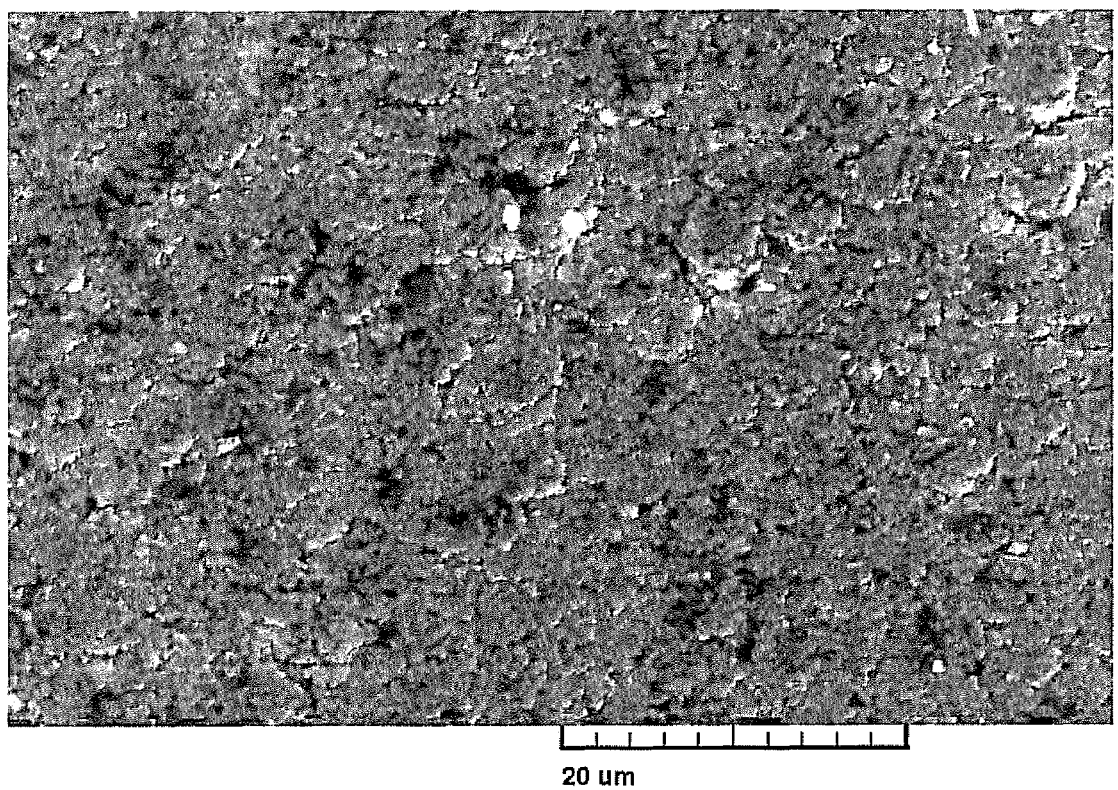
Figure 4:
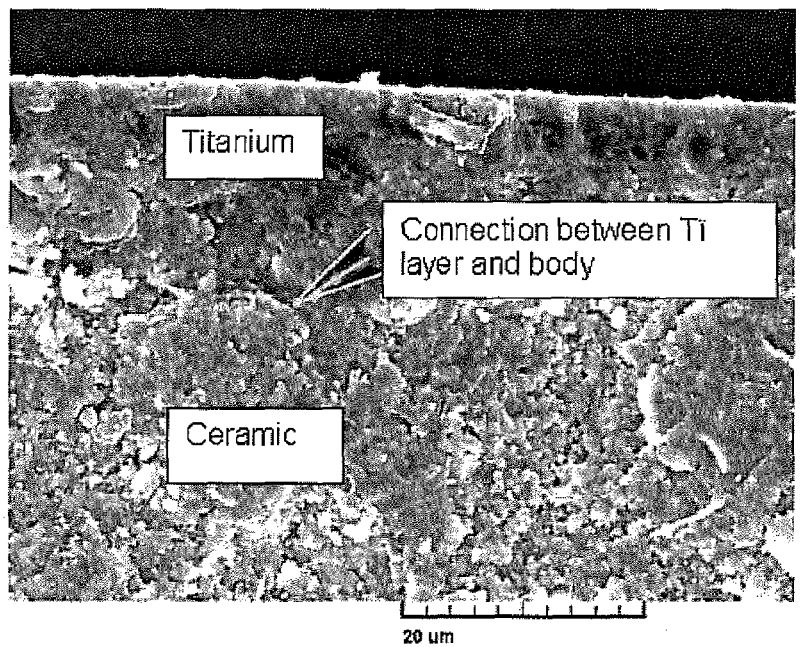
Figure 5:
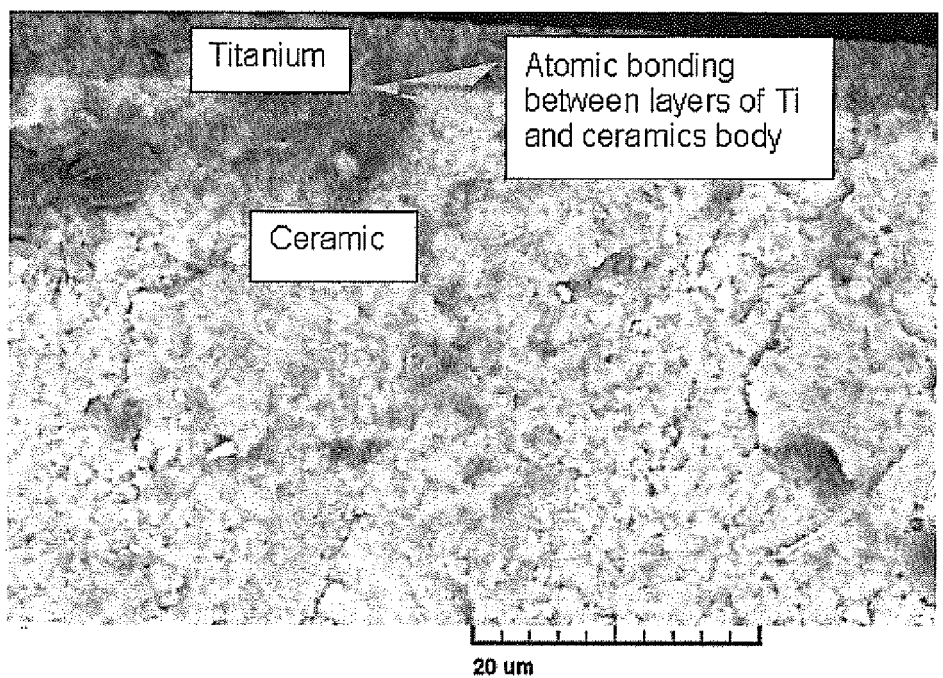
Figure 6:
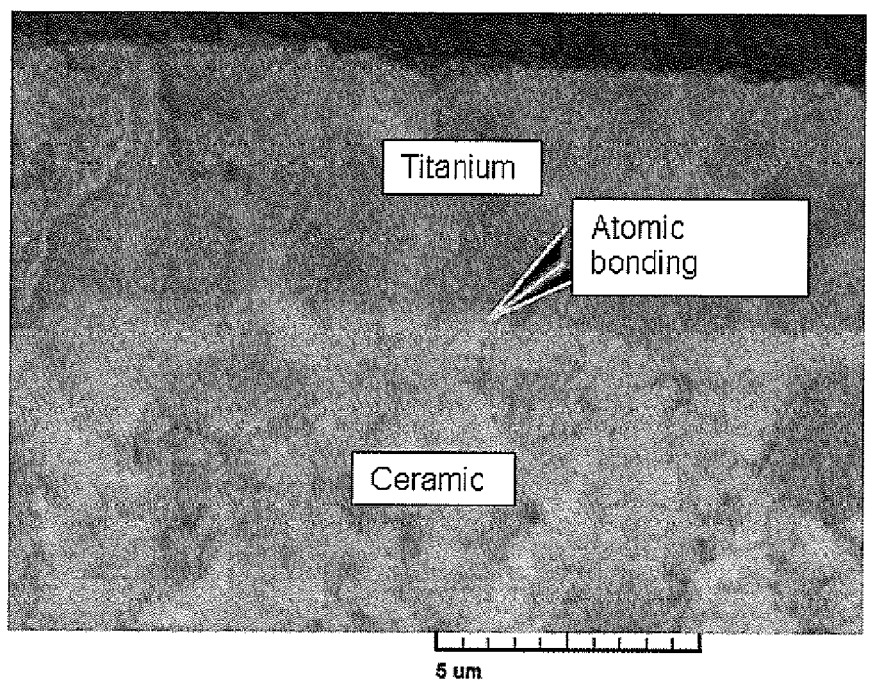
Figure 7:
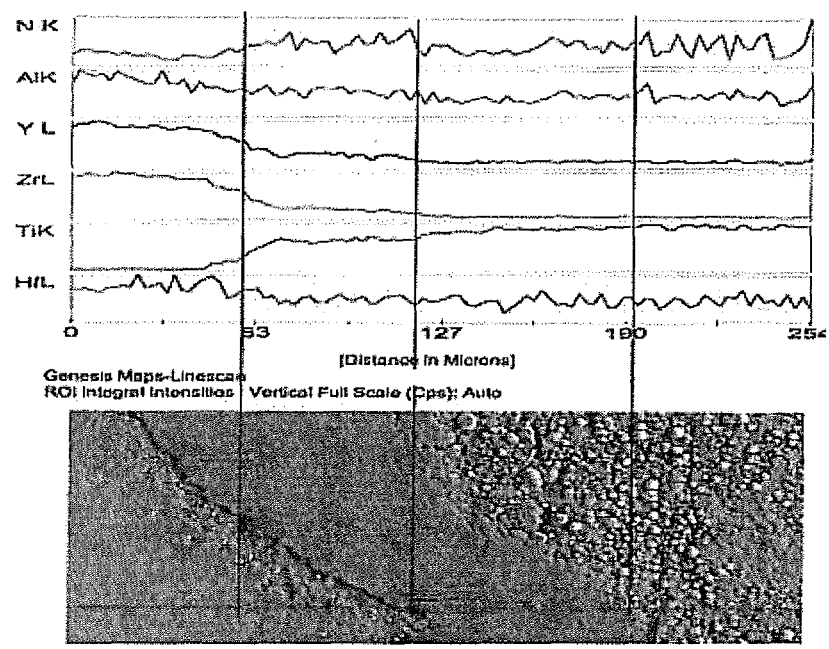
Figure 8:
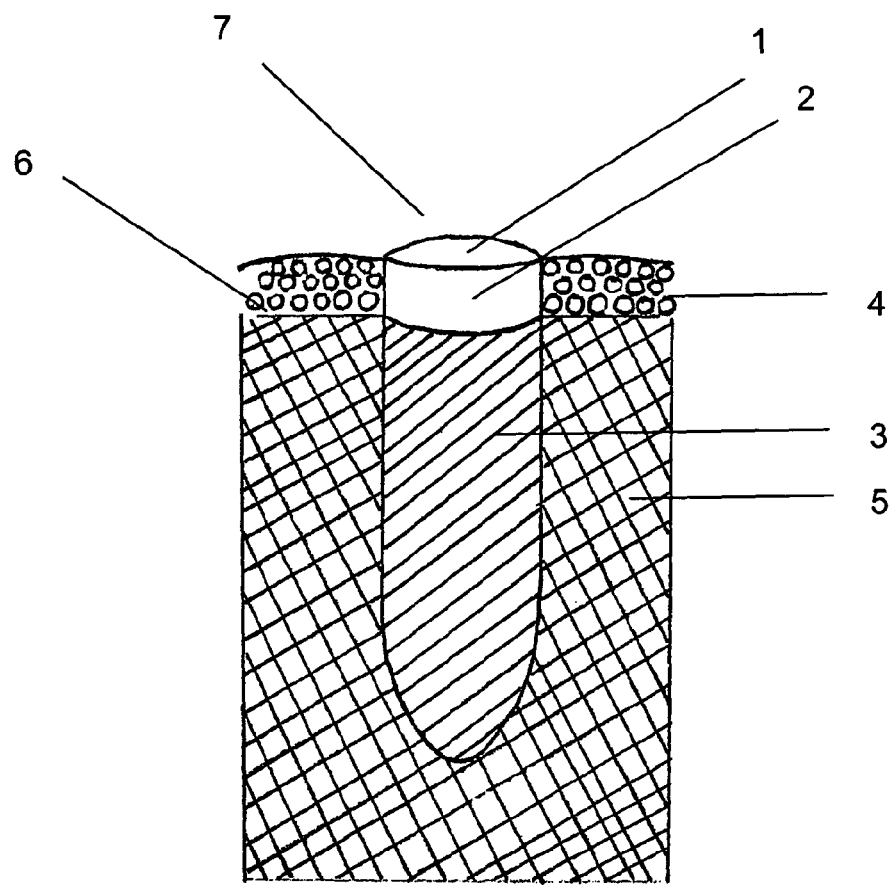
Figure 9:
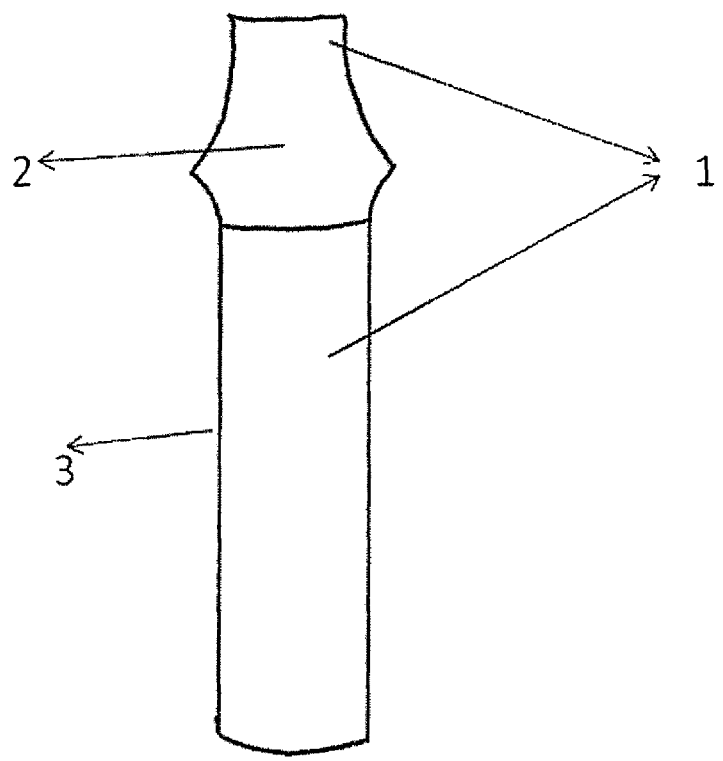
Figure 10:
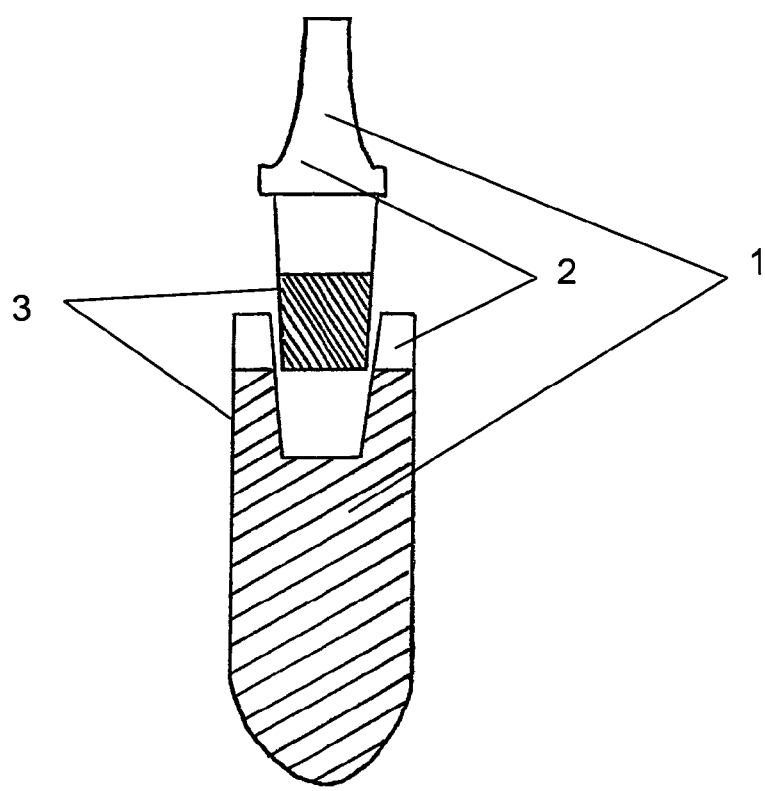
Figure 11:
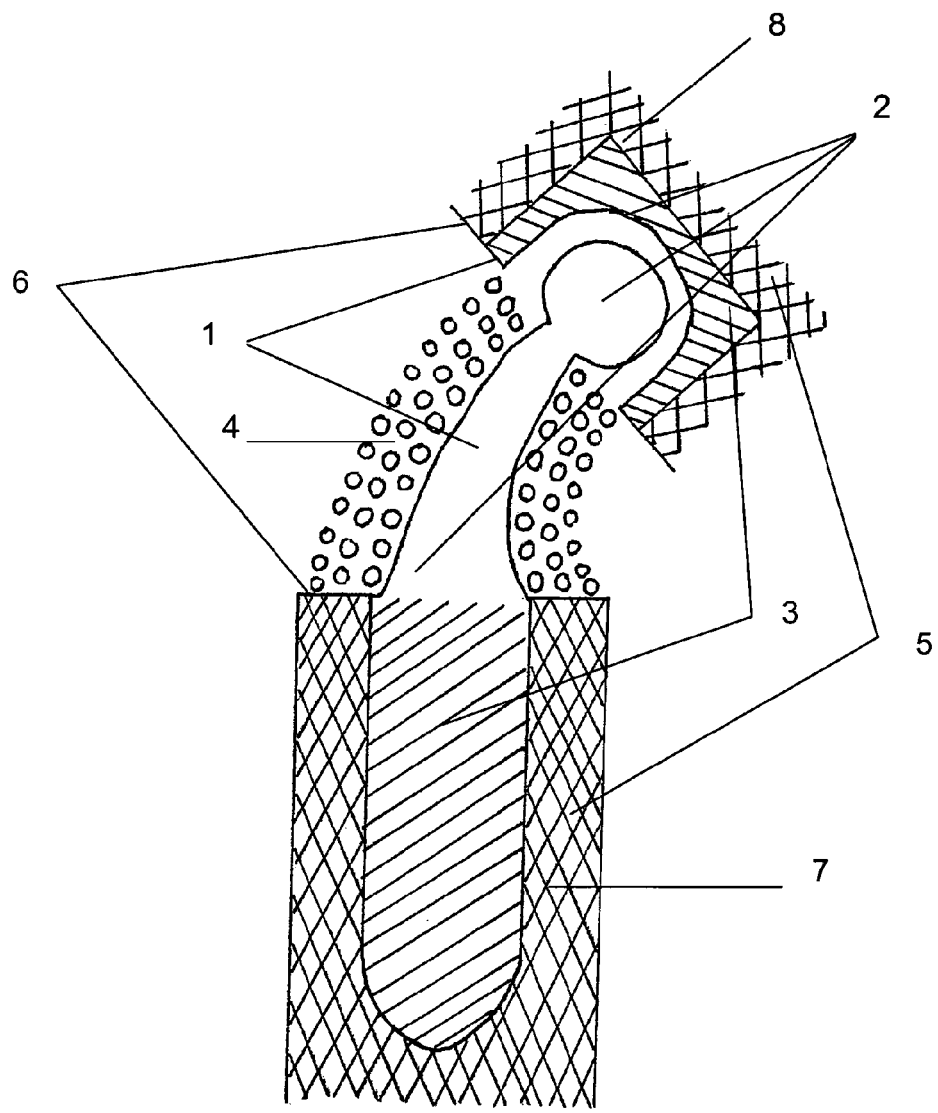
Figure 12:
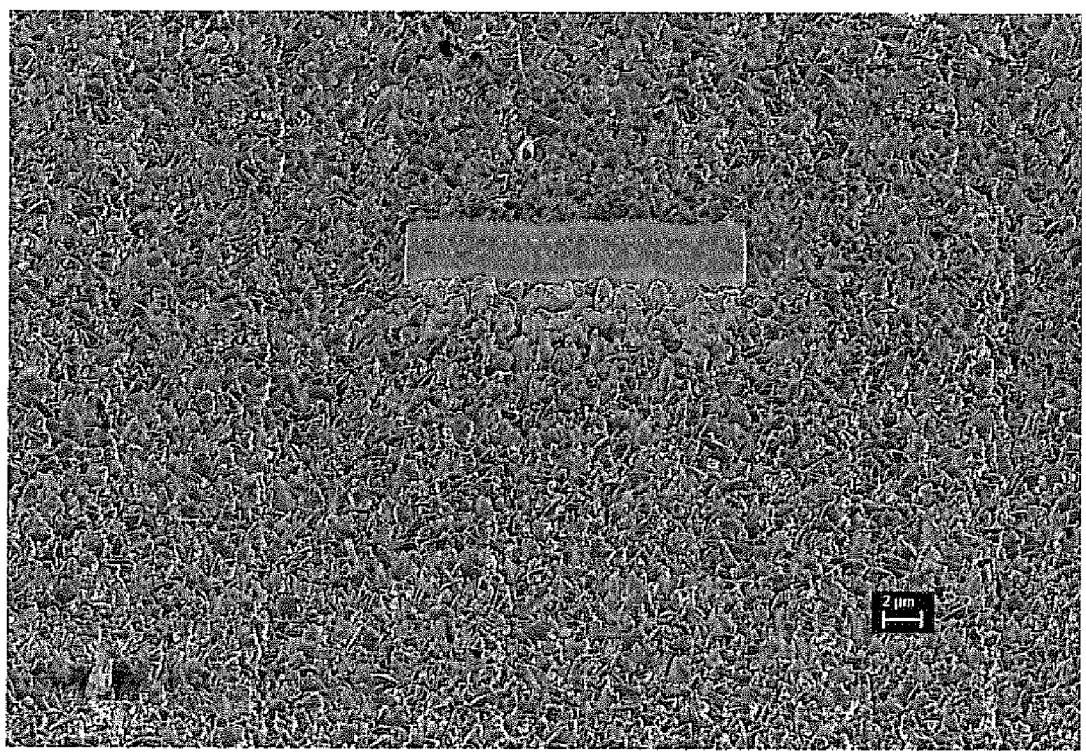
Figure 13:
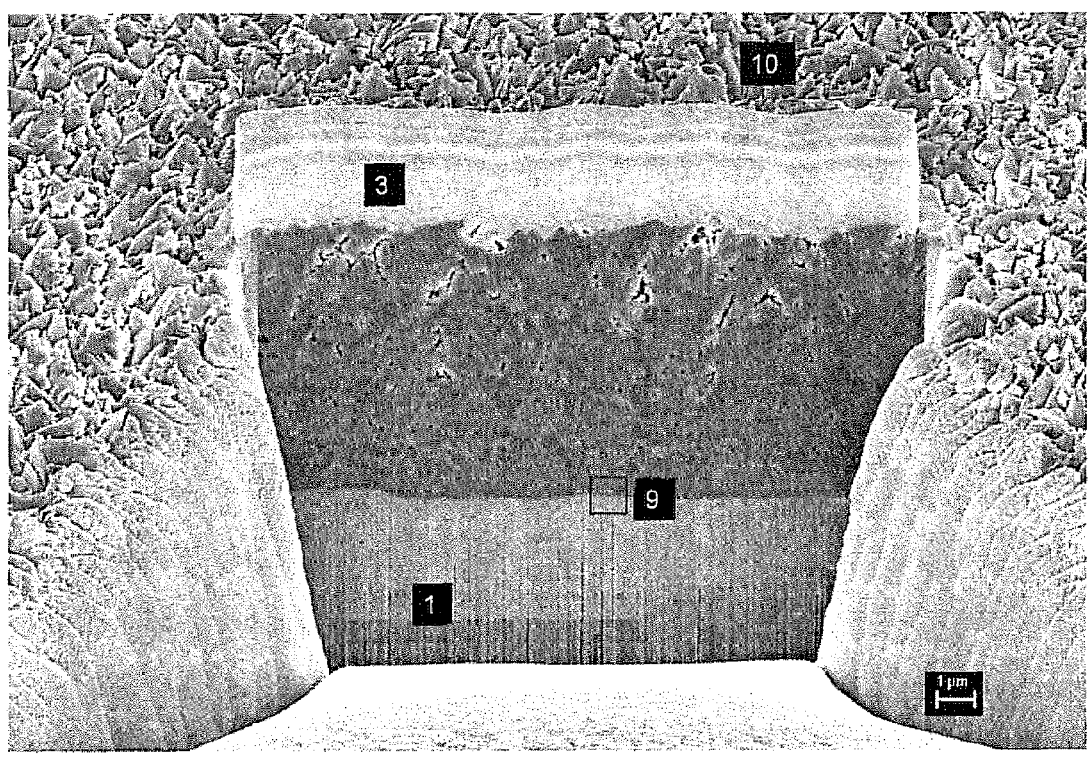
Figure 14:
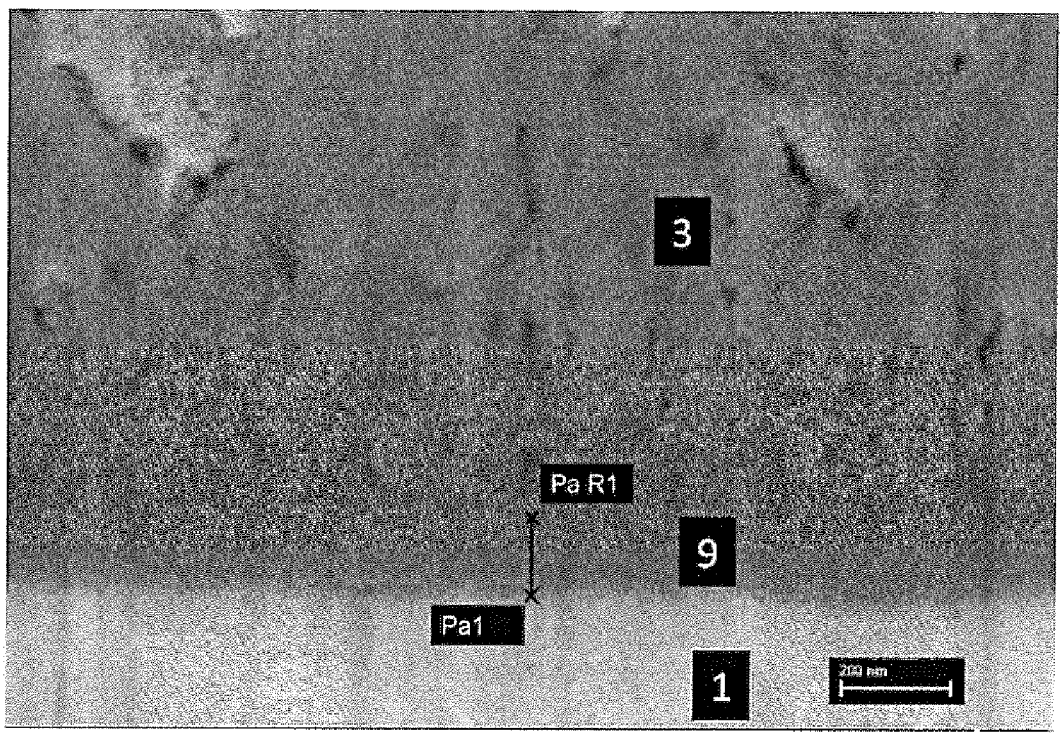
Figure 15:
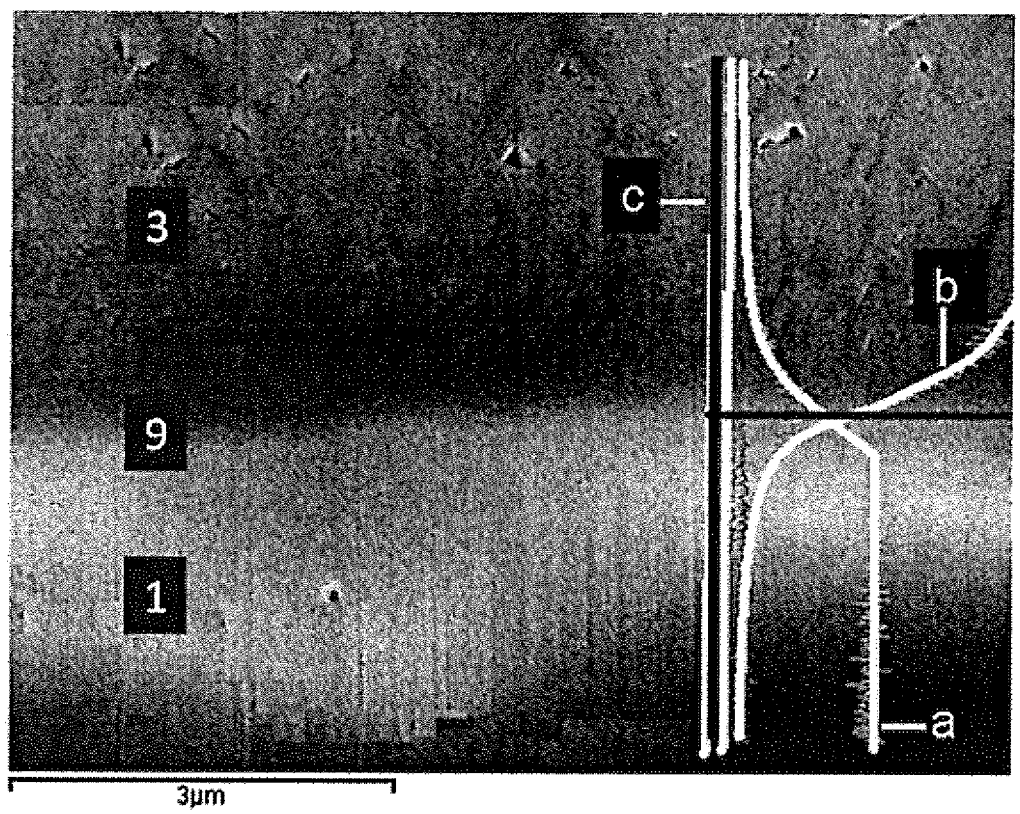

FIG. 1 Test of material by scratching. No material flaked.
FIG. 2 Magnification of FIG. 1
FIG. 3 Scanning electron micrograph (20 µm) of surface.
FIG. 4 Scanning electron micrograph of the ceramic-titanium interface of a titanium-coated ceramic basic body (20 µm)
FIG. 5 Scanning electron micrograph of the fracture surface of the ceramic-titanium interface of a titanium-coated ceramic basic body (20 µm)
FIG. 6 Scanning electron micrograph of the fracture surface of the ceramic-titanium interface of a titanium-coated ceramic basic body (5 µm)
FIG. 7 Dispersive X-ray spectroscopy of the ceramic-titanium interface.
FIG. 8 Schematic drawing of implant-abutment (7). (1) is the zircon body; (2) is the zircon face without coating; (3) is the titanium face (cover with titanium intraossar); (4) tissue; (5) bone; (6) bone at border of implant entry point
FIG. 9 is the same as FIG. 8 but a one piece implant. Schematic drawing of implant-abutment. (1) is the zirconium body; (2) is the zirconium face without coating; (3) is the titanium face (cover with titanium intraossar)
FIG. 10 Two piece implant with abutment, other than FIGS. 8 and 9. Schematic drawing of implant-abutment. (1) is the zirconium body; (2) is the zirconium face without coating; (3) is the titanium face (cover with titanium)
FIG. 11 Example of an artificial hip joint. (1) is the zirconium body; (2) is the zirconium face without coating; (3) is the titanium face (cover with titanium intraossar); (4) tissue; (5) bone; (6) bone at border of implant entry point; 7,8 artificial hip; (7) femur; (8) pelvic bone.
FIG. 12 Scanning electron micrograph (2 µm) of the Titanium surface
FIG. 13 Scanning electron micrograph of the ceramic-titanium interface of a titanium-coated ceramic basic body (1 µm) (1) is the zircon body; (3) is the titanium face; (9) is the atomic bonding of between layers of Ti and ceramics body; (10) is the surface
FIG. 14 Scanning electron micrograph of the ceramic-titanium interface of a titanium-coated ceramic basic body (200 nm), Enlargement of FIG. 13 (1) is the zircon body (3) is the titanium face; (9) is the atomic bonding of between layers of Ti and ceramics body; The Distance from Pa1 to PaR1 is 140.5 nm
FIG. 15 Scanning electron micrograph of the ceramic-titanium interface of a titanium-coated ceramic basic body (3 µm); (1) is the zircon body; (3) is the titanium face; (9) is the atomic bonding of between layers of Ti and ceramics body; (a) is zircon-concentration (b) is Ti-concentration; (c) is $O_2$-concentration; The overlap of the Zircon- and Ti-concentration in the area of interconnection of titanium face and zircon body demonstrates atomic bonding. Concentration of the respective elements has been determined using Energy Dispersive X-ray (EDX) analysis.

DETAILED DESCRIPTION OF THE INVENTION

The present invention relates to a method for the coating of a surface of a ceramic basic body with a titanium compound, comprising the steps of (i) providing a preformed ceramic material; (ii) at least one step of surface activation of said ceramic material using a plasma for plasma-chemical surface preparation wherein the plasma comprises high-energy ions; (iii) at least one step of applying a titanium compound bonding layer to said ceramic material by plasma-supported coating wherein the plasma-supported coating is performed in pulsed and/or non-pulsed fashion; (iv) at least one step of applying a functional titanium compound layer by pulsed plasma-supported coating.

High-energy ions in the context of the present invention, particularly in the context of step (ii) of the coating method, are ions having energies in the range of from 1 MeV to 2.3 MeV.

Preferably the surface activation step (ii) is performed under an inert gas atmosphere. More preferably, the inert gas is a noble gas; most preferably the noble gas is selected from the group of argon, xenon and krypton. Preferably, the high-energy ions are titanium ions. Step (ii) is preferably an ion implantation of titanium ions into the ceramics surface. Preferably the implantation dose is from about $10^{15}$ to $10^{16}$ ions per $cm^2$.

It is preferred that during step (ii) etching of the surface takes place at an etching speed of preferably between 5 and 32 nm/min.

State of the art ion implantation methods are known for the usage in e.g. doping of semi-conductors, increasing the abrasion resistance of metal surfaces, increasing the hardness of culling areas of tools and generally altering the physical and usage properties of technical surfaces. In these cases, after the actual implantation of the ions accelerated to the surface to be treated, a "spurting out" of single atoms from the lattice of the compound to be implanted and the destruction of the lattice structure in the affected area take place. This first step is usually followed by a "curing" treatment, which is carried out at temperatures above around 400° C. for a defined time to "cure" the defects that have arisen during implantation. However, no "curing" step is performed in the methods according to the present invention as the implanted titanium ions stay in the discrete marginal layer and serve for the anchoring of the titanium bonding layer of predefined thickness applied in step (iii) of the method according to the present invention in the ceramic structure. As the coating in the methods according to the present invention takes place at temperatures below the "curing temperature", no "curing" takes place in the basic structure and in the affected marginal layer. The anchoring results in a considerable increase in the adhesive strength of the applied titanium coating. A notable feature of the methods according to the present invention is thus the absence of "curing" by the use of temperatures below the "curing" temperature in the steps following the ion implantation.

The application of the titanium compound bonding layer in step (iii) may take place at temperatures of from 50 to 300° C. Step (iii) may be performed at a partial pressure of from about $10^{-5}$ mbar to about 1 mbar, preferably of from $10^{-5}$ mbar to $10^{-3}$ mbar.

Preferably, the ions implanted in step (ii) are substantially not melt away during steps (iii) and (iv).

The coating method according to the present invention leads to titanium coatings that adhere very tightly to the ceramic basic body. At the interface of the ceramic body and the titanium compound bonding layer, a composite is formed at atomic level between the ceramic basic body and the titanium compound layer.

By the combination of pulsed and non-pulsed plasma-supported coating in step (iii), the properties of the resulting titanium compound bonding layer can be adjusted. Alternating pulsed and non-pulsed schemes may in some embodiments be used. Preferably, only pulsed plasma supported coating is used in step (iii). Variation of the energy used during the plasma-supported coating steps, e.g. by varying the applied voltage or the pulsing scheme, results in a variation of the physical properties of the titanium compound layers.

The titanium compound bonding layer mediates the adherence of the titanium functional layer to the ceramic basic body and thereby provides a good interlocking between the ceramic material of the ceramic basic body and the functional titanium compound layer. The titanium compound bonding layer and the titanium compound functional layer may gradually merge at their interface.

The terms "titanium compound functional layer", "functional titanium compound layer" and "titanium compound-coated surface layer" are used synonymously herein.

The titanium compound bonding layer has a thickness of from 1 nm to 4 µm, from 1 nm to 3 µm, from 1 nm to 2 µm, from 1 nm to 1 µm, from 10 nm to 3 µm, from 100 nm to 3 µm, preferably from 4 nm to 3 µm, more preferably of from 1 µm to 100 µm, most preferably of from 5 µm to 18 µm.

The functional titanium compound layer has a thickness of from 0.1 µm to 200 µm, 0.1 µm to 100 µm, 0.1 µm to 50 µm, more preferably from 0.1 µm to 20 µm, more preferably from 0.1 µm to 15 µm, even more preferably from 0.1 µm to 10 µm, most preferably of from 5 µm to 18 µm.

In particular embodiments of the invention, one or more of the steps of the method are controlled by means of programmable logical control (PLC). The gas flow during any of the steps (ii) to (iv) can be controlled by means of mass flow control (MFC).

The titanium compound according to the present invention is (elementary) titanium, titanium dioxide, titanium nitride, or a titanium alloy. The titanium compound may in some embodiments be a compound of titanium with elements of the $14^{th}$ (e.g. C, Si, Ge, Sn, Pb), $15^{th}$ (e.g. N, P, As, Sb, Bi) or $16^{th}$ (e.g. O, S, Se, Te, Po) group of the periodic table. Preferably, the titanium compound is elementary titanium. Therefore, titanium compound (bonding and functional) layers relate e.g. to titanium layers, titanium dioxide layers, titanium nitride layers or titanium alloy layers, preferably titanium layers. Also mixtures of different titanium compounds may be used.

In a particular embodiment of the invention, the surface of the functional titanium compound layer is nitrated. This results in a hardening of the surface of the functional titanium compound layer. Nitration can for example be achieved by a step of plasma-supported thermo-chemical nitration. This is preferred for hard coatings.

In some preferred embodiments of the invention, the surface of said preformed ceramic material is only partially coated with a titanium compound coating.

In some particular embodiments of the invention, the method additionally comprises a step of applying a microporous titanium compound layer. This results in an enlargement of surface area.

In preferred embodiments of the invention, the titanium compound is biocompatible. Preferably, the functional titanium compound layer is biocompatible. This enables the use of compositions prepared by the methods according to the present invention in medicinal contexts.

The ceramic material according to the present invention may comprise zirconium dioxide (zirconia), aluminium oxide (alumina), titanium dioxide (titania), silicon nitride, yttrium oxide, hafnium oxide, silicon oxide (silica), magnesium oxide (magnesia), cerium oxide, other metal oxides, or metallic glasses, or mixtures thereof. Preferably, the ceramic material is zirconium oxide or comprises zirconium oxide. Zirconium oxide has a white colour and therefore is preferred for the use in dental contexts.

In preferred embodiments of the invention, the preformed ceramic material provided in step (i) is preformed before sintering, i.e. green ceramic material is preformed and then sintered.

"Green ceramic" material in the context of the present invention relates to unsintered ceramic material.

It is preferred in the context of the present invention, that the titanium compound coating described herein is performed on sintered ceramic material, i.e. steps (ii) to (iv) of the method of the present invention are performed on a sintered preformed ceramic material.

Preferably, the ceramic material is preformed before sintering, i.e. the green ceramic material is shaped and preformed. This has the advantage that green ceramic material is relatively soft and easy to shape as compared to the relatively hard ceramic material after sintering. One advantage of the method according to the present invention is thus the possibility to produce individualized (customized) implants at comparably low costs, e.g. shaping the implants using 3D reconstruction techniques to resemble the anatomical structures to be replaced.

For shaping, the green ceramic material can be pressed or may for example be shaped by lathing, milling, drilling or cutting. It is known to a skilled person, that lathing, milling, drilling and cutting machines may be operated manually or under computer numerical control (CNC).

The preformed ceramic material can be mechanically or physically treated before or after sintering, e.g. for surface enlargement. Preferably, such mechanical or physical treatment is performed on the green ceramic material, i.e. before sintering. Mechanical and physical treatment is faster, easier and cheaper than treatment after sintering, e.g. because of less abrasion due to the relatively soft green ceramic material. The performing and shaping of the green ceramic, i.e. before sintering, also enables and/or facilitates the preparation of individually shaped ceramic materials.

"Mechanical" treatment in the context of the present invention comprises inter alia grinding. "Physical" treatment comprises in the context of the present invention inter alia the treatment by a sandblaster, a laser beam or a high pressure water jet.

The sintered ceramic material may also be chemically treated, e.g. chemically treated by an acid or a mixture of acids. Such an acid or acid mixture may be selected from the group consisting of phosphoric acid, sulphuric acid, hydrochloric acid, hydrofluoric acid, nitric acid, nitric acid/hydrochloric acid mixture or hydrochloric acid/sulphuric acid mixture.

Thus, in a particular embodiment of the invention, the method additionally comprises the step of increasing to surface area of said functional titanium compound layer by chemically, mechanically or physically treating the functional titanium compound layer. An enlarged surface can improve for example the osseo-integration when titanium-coated ceramic material is used in medicinal contexts, e.g. as an implant.

In some embodiments of the invention, the method comprises a step of coating the titanium compound-coated surface layer (i.e. the functional titanium compound layer) with an additional layer of a biocompatible material and/or an additional bioactive surface layer.

The biocompatible material is in a preferred embodiment selected from the group consisting of hydroxylapatite and tricalciumphosphate and the bioactive surface layer comprises a composition selected from the group of antibiotic, growth factor, peptide, fibronectin and anti-inflammator. Hydroxylapatite and tricalciumphosphate are osseoactive, i.e. they mediate and/or facilitate osseointegration.

The antibiotic in the context of the present invention can for example be selected from the group of Amikacin, Gentamicin, Kanamycin, Neomycin, Netilmicin, Paromomycin, Streptomycin, Tobramycin, Cephalosporins, Fluoroquinolone antibiotics, Azithromycin, Erythromycin, Clarithromycin, Dirithromycin, Roxithromycin, Telithromycin, Penicillins, Ampicillin, Sulfonamides, Tetracycline antibiotics, Clindamycin, Metronidazole, and Vancomycin.

The growth factors in the context of the present invention can for example be selected from the group of Transforming growth factor beta (TGF-β), Granulocyte-colony stimulating factor (G-CSF), Granulocyte-macrophage colony stimulating factor (GM-CSF), Nerve growth factor (NGF), Neurotrophins, Platelet-derived growth factor (PDGF), Erythropoietin (EPO), Thrombopoietin (TPO), Myostatin (GDF-8), Growth differentiation factor-9 (GDF9), Acidic fibroblast growth factor (aFGF or FGF-1), Basic fibroblast growth factor (bFGF or FGF-2), Epidermal growth factor (EGF), Hepatocyte growth factor (HGF), Insulin-like growth factors (IGFs), and Bone Morphogenetic Proteins (BMPs).

The anti-inflammator in the context of the present invention can for example be selected from the group of glucocorticoids, corticosteroids and non-steroidal anti-inflammatory drugs (e.g. ibuprofen, aspirin and naproxen).

A peptide can for example be a bioactive peptide such as RGD.

In particular embodiments, said bioactive surface layer comprises osseous stem cells or chondral stem cells or a mixture thereof. These stem cells improve osseointegration of the titanium-coated ceramic materials according to the present invention.

The present invention also relates to the use of the above described methods for the preparation of a medicinal implant.

"Medicinal" in the context of the present invention relates to the fields of human medicine, dentistry, veterinary medicine and dental veterinary medicine. Therefore, medicinal implants also comprise e.g. implants and dental implants for humans and animals.

The medicinal implants are in preferred embodiments of the invention selected from the group consisting of dental implant, hip implant, epithesis, artificial joint and prosthesis.

A medicinal implant in the context of the present invention is a medicinal device prepared to replace and act as a missing biological structure in a human or animal body. A prosthesis is an artificial extension that replaces a missing (e.g. because of a disease, an accident or an amputation) body part, whereas an epithesis has primarily a cosmetic function (e.g. as an artificial eye or ear). Medicinal implants and in particular prostheses can be used to replace biological structures, such as bones or part of bones, in nearly all parts of the body, e.g. scull, teeth, (upper and lower) arm, elbow, (upper and lower) leg, hip, toes, fingers, knee, spine, joints and the like. Also hearing aids, artificial limbs, replacement joints and hair prostheses (wigs) are medicinal implants in the context of the present invention. Also implants for the anchoring of other implants such as protheses, epitheses and wigs are within the scope of the invention. In very particular embodiments, hearing aids may be integrated into other implants.

Implants and dental implants are in some embodiments of the present invention multi- or single-part implants.

In preferred embodiments of the invention, only the part(s) of the medicinal implant, and dental implant in particular, that has/have contact with a bone (i.e. the "anchoring part") is titanium compound-coated.

The dental implant is in a particular embodiment a one-piece implant or a two-piece implant.

The dental implant may comprise a screw thread. Preferably, the dental implant comprises an anchoring part for anchoring said implant in the bone and a mounting part for receiving a prosthetic superstructure, wherein only the anchoring part is coated with the biocompatible titanium compound. In one particular embodiment of a two-piece dental implant, the surface area on one part (e.g. on the abutment) which makes contact to the other part (i.e. a "plug-and-socket connection" between implant and abutment), is titanium-coated. In this case, no screw connection is necessary between the two parts because a good fitting accuracy can be reached, resulting in a high stability of the connection.

In one preferred embodiment, the implant is an artificial joint and the preformed ceramic material is monolithic. In some cases at least one part of the artificial joint is titanium compound coated. In some artificial joints, a pair of two parts which can slide relative to each other is present. In some of such cases, the surface of only one part is titanium-compound coated. In other cases the surface of both parts is coated or at least coated in part. E.g. in the case of a "ball-and-socket" artificial hip joint (i.e. an artificial hip replacement), in which the ball of the femoral component makes contact to the socket of the joint, only the part of the surface of the joint implant which makes contact to the ball of the joint is coated or vice versa. This has the advantage that the titanium cup which is present in some state-of-the-art hip replacements, can be omitted according to the present invention. In general, where two monolithic ceramic implants make contact to each other, one or both blocks may be titanium coated according to the present invention. Also where a ceramic implant makes contact to another part that is made of other materials such as polyethylene, only the area that is involved in the contact is coated with a biocompatible titanium layer.

The biocompatible titanium coating on parts of artificial joints, particularly hip joints, can avoid squeaking or other unwanted noises which may occur during movement of these joints. Particularly the coating of the sphere in the artificial hip joint may be used to reduce squeaking noises and the titanium coating serves as a lubricant.

Where the implant is a multipart-implant, e.g. a two-part-implant (such as a "plug-and-socket connection" in an artificial hip joint), in some embodiments only one part (e.g. the part inserted into the sphere in an artificial hip joint, is coated with a biocompatible titanium compound layer. For example, where plug connections are concerned, only the plug in one part is coated and the borehole in another part is not coated. An example for such an embodiment is an artificial hip joint.

Also within the scope of the present invention is the use of the methods described herein for the preparation of a projectile comprising a ceramic body and at least a titanium layer.

Such a titanium compound coated ceramic projectile has a hard ceramic body and a relatively soft titanium compound surface. This allows a better penetration of the target. In this case the titanium layer serves as a lubricant.

The projectile is e.g. a munitions projectile. The term "projectile" herein also refers to all kinds of ballistic bodies, e.g. rockets, grenades, munitions for firearms, crossbows and the like.

In general the present invention also relates to a composition comprising a ceramic material coated with a titanium compound, obtainable with any of the methods described herein.

Such a composition may in some embodiments also comprise an additional layer of diamond-like carbon (DLC). DLC is an amorphous hard carbon.

In some embodiments the composition may comprise one or more additional metal coating layers such as gold, silver, platinum, aluminium, copper, iron, nickel, tin, tantalum, zinc and/or chromium and/or alloys such as steel or bronze.

Finally, also within the present invention is a ceramic composition comprising a ceramic part and at least a first biocompatible titanium compound layer, wherein said titanium compound layer has a thickness of from 0.1 to 1 mm, preferably 0.1 to 100 µm, more preferably of from 0.5 to 50 µm, and wherein the bonding strength between the ceramic part and said at least first titanium layer when measured by applying a load at a stretching speed of 1 mm/minute until the test piece is broken, is above 100 MPa, preferably above 200 MPa, more preferably above 700 MPa, even more preferably above 900 MPa, most preferably above 1200 MPa. Most preferably, the titanium layer breaks under these conditions only upon breakage of the ceramic part.

EXAMPLES

A homogenous film of pure titanium was used as specified in the description. The body is made of ceramic. The film on top is pure titanium with a thickness of 6-16 µm.

Chemical analysis shows the following ingredients in the product.

TABLE I

| Body | | | Layer on body | | |
|---|---|---|---|---|---|
| Phase | Massen % | Mol % | Element | Massen % | Mol % |
| $ZrO_2$ | 90.89 | 94.84 | Ti | 89.21 | 79.92 |
| $Y_2O_3$ | 6.32 | 3.6 | O | 6.49 | 16.09 |
| $Hf_2O_3$ | 2.07 | 0.66 | N | 3.27 | 9.26 |
| $Al_2O_3$ | 0.71 | 0.9 | Zr | 0.64 | 0.28 |
| | | | Al | 0.26 | 0.39 |
| | | | Y | 0.14 | 0.06 |

It was not possible to disassemble the titanium layer from the body.

Also monolithic hip joints with titanium layers were tested.

One of the prototypes was used for analysing the break point as well as the flaking properties of the layer. The layers were analysed using the scanning electron microscopy.

One can observe a homogenous interlocking of the body and the layer (Ti). No flaking was observable. See also appended figures. In fact removal of the titanium coating from the ceramics body was only possible under conditions where the ceramic body broke.

The invention claimed is:

1. A method of preparing a projectile, the projectile having a ceramic body and at least one titanium layer, by coating a surface of a ceramic basic body with a titanium compound, the method comprising:
   (i) providing a preformed ceramic material;
   (ii) activating said ceramic material using a plasma for plasma-chemical surface preparation wherein the plasma comprises high-energy ions;
   (iii) applying a titanium compound bonding layer to said ceramic material by plasma-supported coating wherein the plasma-supported coating is performed in a pulsed and/or non-pulsed fashion;
   (iv) applying a functional titanium compound layer by pulsed plasma-supported coating where the projectile is a rocket, grenade, or a munition.

2. The method according to claim 1, wherein the surface of the ceramic basic body is only partially coated with a titanium compound.

3. The method according to claim 2, wherein the functional titanium compound layer is nitrated.

4. The method according to claim 2, wherein said ceramic material comprises zirconium dioxide, alumina, titanium dioxide, silicon nitride or metallic glass, or mixtures thereof.

5. The method according to claim 4, wherein the preformed ceramic material provided in step (i) is preformed before sintering.

6. The method according to claim 4, further comprising increasing the surface area of the functional elemental titanium layer by chemically, mechanically or physically treating the functional elemental titanium layer.

7. The method according to claim 2, wherein each titanium compound is independently selected from the group consisting of titanium, titanium oxide, and titanium alloy.

8. The method according to claim 2, wherein the preformed ceramic material provided in step (i) is preformed before sintering.

9. The method according to claim 2, further comprising applying a microporous titanium compound layer.

10. The method according to claim 2, additionally comprising the step of increasing the surface area of said functional titanium compound layer by chemically, mechanically or physically treating the functional titanium compound layer.

11. The method according to claim 2, wherein the preformed ceramic material provided in step (i) is preformed before sintering.

12. The method according to claim 1, wherein the surface of the ceramic basic body is totally coated with a titanium compound.

13. The method according to claim 1, wherein the functional titanium compound layer is nitrated.

14. The method according to claim 1, wherein said ceramic material comprises zirconium dioxide, alumina, titanium dioxide, silicon nitride or metallic glass, or mixtures thereof.

15. The method according to claim 1, wherein each titanium compound is independently selected from the group consisting of titanium, titanium oxide, and titanium alloy.

16. The method according to claim 1, wherein the preformed ceramic material provided in step (i) is preformed before sintering.

17. The method according to claim 1, further comprising applying a microporous titanium compound layer.

18. The method according to claim 1, additionally comprising the step of increasing the surface area of said functional titanium compound layer by chemically, mechanically or physically treating the functional titanium compound layer.

19. A method of preparing a projectile, the projectile having a ceramic body and at least one titanium layer, by coating a surface of a ceramic basic body with elemental titanium, the method comprising:
 (i) providing a preformed green ceramic material;
 (ii) sintering the preformed ceramic material;
 (iii) activating said ceramic material using a plasma for plasma-chemical surface preparation wherein the plasma comprises high-energy ions;
 (iv) applying an elemental titanium bonding layer to said ceramic material by plasma-supported coating wherein the plasma-supported coating is performed in a pulsed or non-pulsed fashion; and
 (v) applying a functional elemental titanium layer by pulsed plasma-supported coating where the projectile is a rocket, grenade, or a munition.

20. The method according to claim 19, further comprising nitrating the functional elemental titanium layer.

* * * * *